US012031181B2

(12) United States Patent
Zhang et al.

(10) Patent No.: US 12,031,181 B2
(45) Date of Patent: Jul. 9, 2024

(54) QUANTITATIVE SCORE OF HLA DIVERSITY

(71) Applicant: ILLUMINA, INC., San Diego, CA (US)

(72) Inventors: Bochao Zhang, La Jolla, CA (US); Shile Zhang, San Diego, CA (US)

(73) Assignee: ILLUMINA, INC., San Diego, CA (US)

( * ) Notice: Subject to any disclaimer, the term of this patent is extended or adjusted under 35 U.S.C. 154(b) by 312 days.

(21) Appl. No.: 16/838,832

(22) Filed: Apr. 2, 2020

(65) Prior Publication Data

US 2020/0318187 A1 Oct. 8, 2020

Related U.S. Application Data

(60) Provisional application No. 62/830,297, filed on Apr. 5, 2019.

(51) Int. Cl.

| | |
|---|---|
| ***C12Q 1/6881*** | (2018.01) |
| ***A61B 5/00*** | (2006.01) |
| ***G16B 20/20*** | (2019.01) |
| ***G16B 20/40*** | (2019.01) |
| ***G16H 20/40*** | (2018.01) |
| ***G16H 50/30*** | (2018.01) |

(52) U.S. Cl.

CPC ............ *C12Q 1/6881* (2013.01); *A61B 5/444* (2013.01); *G16B 20/20* (2019.02); *G16B 20/40* (2019.02); *G16H 20/40* (2018.01); *G16H 50/30* (2018.01)

(58) Field of Classification Search

None

See application file for complete search history.

(56) References Cited

U.S. PATENT DOCUMENTS

2019/0008583 A1 * 1/2019 Gallagher .......... A61N 1/36096

FOREIGN PATENT DOCUMENTS

| | | | | |
|---|---|---|---|---|
| CN | 105189779 A | 12/2015 | | |
| CN | 106164289 A | 11/2016 | | |
| CN | 108624650 A | 10/2018 | | |
| JP | 2018134038 A | 8/2018 | | |
| WO | WO-2016145294 A1 * | 9/2016 | ............. | A61K 31/46 |

OTHER PUBLICATIONS

Boegel et al. HLA typing from RNA-SEQ sequence reads Genome Medicine vol. 4, article 102 (Year: 2012).*

Samstein et al. Tumor mutational load predicts survival after immunotherapy across multiple cancer types Nature Genetics vol. 51, pp. 202-206 (Year: 2019).*

Seidel et al. Anti-PD-1 and Anti-CTLA-4 Therapies in Cancer: Mechanisms of Action, Efficacy, and Limitations frontiers in Oncology vol. 8, article 86 (Year: 2018).*

Sidaway HLA-1 genotype influences response to checkpoint inhibitors Nature Reviews clinical oncology vol. 15, p. 66 (Year: 2018).*

Madden et al. "HLA testing in the molecular diagnostic laboratory." Virchows Archiv: European Journal of Pathology. 2019. vol. 474 , pp. 139-147. (Year: 2019).*

Buhler et al. "HLA DNA Sequence Variation among Human Populations: Molecular Signatures of Demographic and Selective Events." PLoS One, vol. 6(2): e14643. doi:10.1371/journal.pone.0014643, pp. 1-16. (Year: 2011).*

Li et al. "The landscape of antigen-specific T cells in human cancers." bioRxiv, 2018, doi: https://doi.org/10.1101/459842, pp. 1-42. (Year: 2018).*

Ogishi. "Prioritizing putatively etiological T cell epitopes across autoimmune diseases." bioRxiv, doi: https://doi.org/10.1101/580126, pp. 1-25; Supplementary Material, pp. 1-4. (Year: 2019).*

Karaca et al. "Genetic diversity of disease-associated loci in Turkish population." Journal of Human Genetics, vol. 60, pp. 193-198. (Year: 2015).*

Rosenwald et al. "The use of molecular profiling to predict survival after chemotherapy for diffuse large-B-cell lymphoma." New England Journal of Medicine, vol. 346, No. 25, pp. 1937-1947. (Year: 2002).*

Herbst et al. "Pembrolizumab versus docetaxel for previously treated, PD-L1-positive, advanced non-small-cell lung cancer (Keynote-010): a randomized controlled trial." Lancet, vol. 387, pp. 1540-1550. (Year: 2016).*

Tobin et al. "The importance of molecular markers for diagnosis and selection of targeted treatments in patients with cancer." Journal of Internal Medicine, 2015, vol. 278, pp. 545-570. (Year: 2015).*

Harding et al. "Biomarkers: What role do the play (if any) for diagnosis, prognosis and tumor response prediction for Hepatocellular Carcinoma?." Digestive Diseases and Sciences, 2019, vol. 64, pp. 918-927. (Year: 2019).*

International Search Report and Written Opinion dated Sep. 16, 2020 in ; PCT/US2020/026394.

Boegel, et al., In Silico HLA Typing Using Standard RNA-Seq Sequence Reads, Methods in Molecular Biology, vol. 1310, pp. 247-258, 2015.

Chowel, et al., Patient HLA class I genotype influences cancer response to checkpoint blockade immunotherapy, Science, vol. 359, No. 6375, pp. 582-587, 2018.

* cited by examiner

*Primary Examiner* — John S Brusca

*Assistant Examiner* — Steven W. Bailey

(74) *Attorney, Agent, or Firm* — Knobbe, Martens, Olson & Bear, LLP

(57) ABSTRACT

Provided herein are systems and methods for quantitating the HLA diversity in a solid tissue or circulating tumor DNA sample that is predictive of a patient's responsiveness to immune checkpoint inhibitory therapies.

24 Claims, 6 Drawing Sheets

HLA-A

HLA-B

HLA-C

QUANTITATIVE SCORE OF HLA DIVERSITY

REFERENCE TO RELATED APPLICATIONS

This application claims priority to U.S. Provisional Patent Application No. 62/830,297, filed Apr. 5, 2019, the disclosure of which is hereby incorporated by reference in its entirety herein.

BACKGROUND

Field

The present disclosure is related to HLA allele diversity and quantifying HLA allele diversity.

Description of the Related Art

The Human leukocyte antigen (HLA) system or complex is a gene complex encoding the major histocompatibility complex (MHC) proteins in humans. The major histocompatibility complex (MHC) is a set of cell surface proteins essential for the acquired immune system to recognize foreign molecules in vertebrates, which in turn determines histocompatibility. The main function of MHC molecules is to bind to antigens derived from pathogens and display them on the cell surface for recognition by the appropriate T-cells. MHC molecules are responsible for the regulation of the immune system in humans. The MHC determines compatibility of donors for organ transplant, as well as one's susceptibility to an autoimmune disease via cross-reacting immunization. Thus, HLA plays an important role in infection, autoimmune disease and cancer.

SUMMARY

In some embodiments, a method of quantifying a diversity of at least one HLA allele pair in a subject comprises obtaining DNA sequences of one or more HLA allele pairs in the subject, comparing the DNA sequences of the one or more HLA allele pairs to obtain alignment scores, obtaining a distribution of the alignment scores for the one or more HLA allele pairs, and determining a percentile score for the at least one HLA allele pair relative to the distribution of the alignment scores for all HLA allele pairs.

In some embodiments, a method of quantifying a diversity of at least one HLA allele pair in a subject further comprising comparing the percentile score to a first predetermined threshold.

In some embodiments of a method of quantifying a diversity of at least one HLA allele pair in a subject, the at least one HLA allele pair comprises any pair of HLA A, B, C, E, F, G, H, J, K, L, DP, DQ, and DR alleles.

In some embodiments of a method of quantifying a diversity of at least one HLA allele pair in a subject, if the percentile score is equal to or greater than the first predetermined threshold, the subject is recommended a first treatment.

In some embodiments of a method of quantifying a diversity of at least one HLA allele pair in a subject, if the percentile score is less than the first predetermined threshold, the subject is recommended a second treatment.

In some embodiments, a method of quantifying a diversity of at least one HLA allele pair in a subject further comprises, determining an expression level of the one or more HLA allele pairs, obtaining an expression level score of the at least one HLA allele pair relative to the expression levels of the one or more HLA allele pairs, determining a weighted percentile score for the at least one HLA allele pair, based on the expression level score of the at least one HLA allele pair, relative to the distribution of the alignment scores for the one or more HLA allele pairs, comparing the weighted percentile score to a second predetermined threshold. In some embodiments, if the weighted percentile score is equal to or greater than the second predetermined threshold, the subject is recommended a first treatment.

In some embodiments, if the weighted percentile score is less than the second predetermined threshold, the subject is recommended a second treatment.

In some embodiments, the first predetermined threshold is about 75%.

In some embodiments, the second predetermined threshold is about 75%.

In some embodiments, the first treatment comprises an ICI.

In some embodiments, the second treatment comprises a non-ICI.

In some embodiments, if first predetermined threshold is 50%, then the subject is further recommended a first additional treatment.

In some embodiments, if the second predetermined threshold is 50%, then the subject is further recommended a second additional treatment.

In some embodiments, the expression level is expression level of RNA, expression level of protein or both.

In some embodiments of a method of quantifying a diversity of at least one HLA allele pair, the quantifying is repeated over time to determine if there is a change in the percentile score relative to the first predetermined threshold.

In some embodiments of a method of quantifying a diversity of at least one HLA allele pair, the quantifying is repeated over time to determine if there is a change in the percentile score relative to the second predetermined threshold.

In some embodiments of a method of quantifying a diversity of at least one HLA allele pair, the quantifying comprises an assessment of TCR clonality.

In some embodiments, a method of determining the predicted efficacy of a cancer treatment in a patient comprises calculating a hazard ratio of HLA allele pairs in the patient, wherein the hazard ratio reflects the allelic diversity of the HLA allele pairs in the patient, comparing the hazard ratio to a predetermined threshold, wherein a hazard ratio above the predetermined threshold indicates that the patient is predicted to have a high efficacy for a cancer treatment, and a hazard ratio below the predetermined threshold indicates that the patient is predicted to have a low efficacy for a cancer treatment.

In some embodiments, a method of determining the predicted efficacy of a cancer treatment in a patient further comprises measuring a tumor burden score for the patient and comparing the tumor burden score to a predetermined threshold as a factor in determining the efficacy of a cancer treatment.

DETAILED DESCRIPTION

Embodiments of the present disclosure relate to systems and methods for quantitating the diversity of HLA allelic variants in a biological sample from a patient. In some embodiments, the systems and methods are for quantitating the HLA diversity in a solid tissue or circulating tumor DNA sample. In some embodiments, the systems and methods are for quantitating the HLA diversity in a solid tissue or circulating tumor DNA sample that is predictive of a patient's responsiveness to therapies to treat such indications. In some embodiments, the systems and methods are for quantitating the HLA diversity in a solid tissue or circulating tumor DNA sample that is predictive of a patient's responsiveness to anti-tumor therapies. In some embodiments, the systems and methods are for quantitating the HLA diversity in a solid tissue or circulating tumor DNA sample that is predictive of a patient's responsiveness to immune checkpoint inhibitory therapies.

As discussed below, each HLA allele is made up of various domains. Some embodiments relate to systems and methods for comparing the diversity of a patient's HLA domains to calculate the variation between each domain on every HLA allele. For example, one patient suffering from a tumor may have two HLA alleles with domains that are 95% identical. Another patient suffering from a tumor may have two HLA alleles with domains that are 15% identical. In one embodiment, the system may determine that the patient with the HLA allelic variants that are only 15% identical, and thus more diverse from one another, may have a higher likelihood of a successful cancer treatment as compared to the tumor patient with less diverse HLA allele domains. In one example, the cancer treatment may be a CAR-T treatment where the patients T-cells are removed and genetically altered to attach the tumor. Patients having a greater diversity of HLA allelic variants may have a more successful CAR-T treatment as compared to patients how have less diversity between their HLA alleles.

The HLA class I genes are a component of the human major histocompatibility complex (MHC). The class I genes consist of the three classical genes encoding the major transplantation antigens HLA-A, HLA-B and HLA-C and seven non-classical class I genes. HLA-E. HLA-F, HLA-G. HLA-H, HLA-J. HLA-K, and HLA-L.

Figures 1A, 1B, 1C:
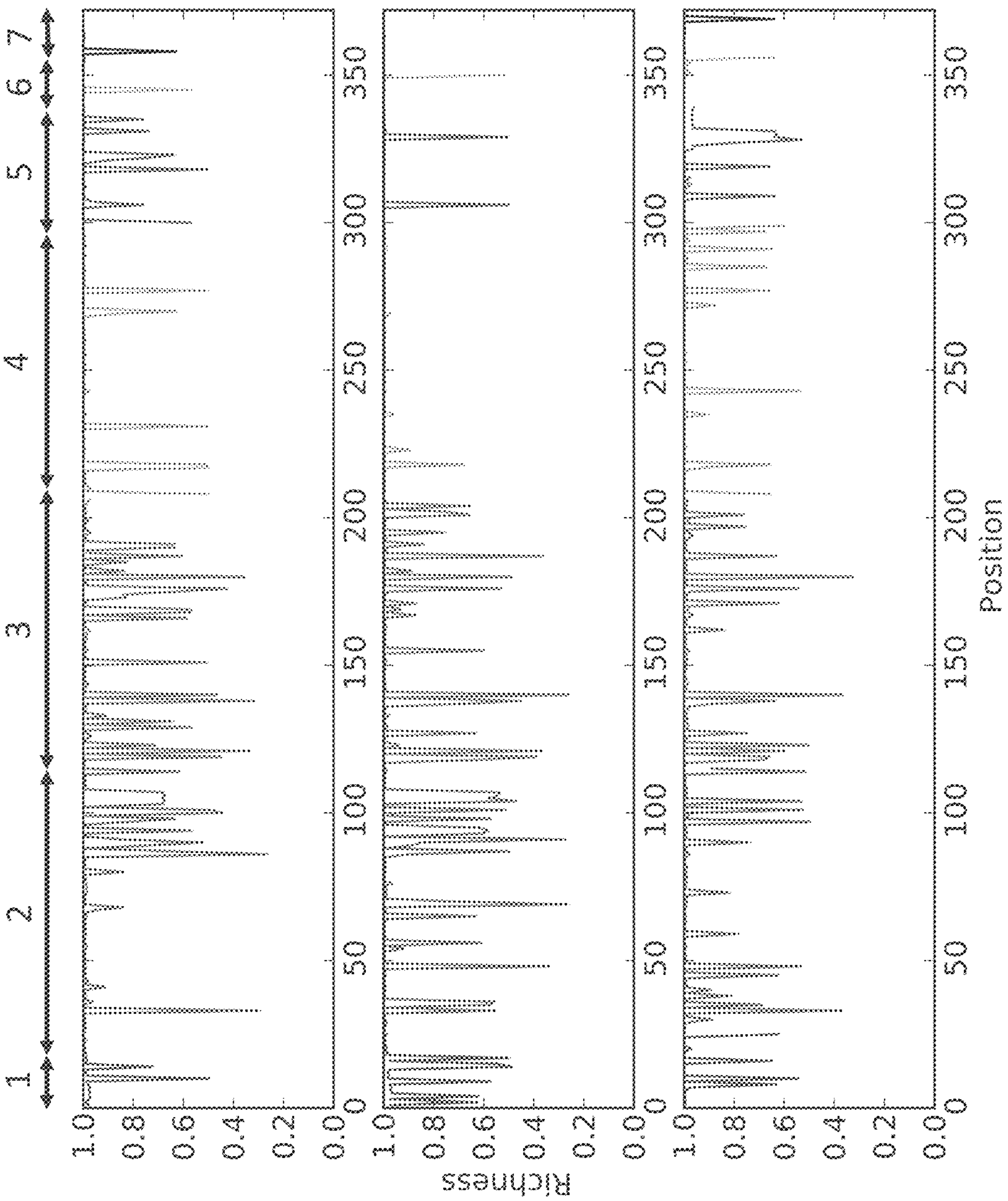
FIGS. 1A-1C show amino acid diversity at each position for protein encoded by HLA-A (FIG. 1A), HLA-B (FIG. 1B), and HLA-C (FIG. 1C), respectively. A lower score on the graph indicates a greater diversity. The numbers at the top of FIG. 1A indicate the various protein domains of the HLA proteins based on their amino acid position.

The HLA complex is located on the short arm of chromosome 6. The genes belonging to HLA class I encode the MHC class I proteins and the genes belonging to HLA class II encode the MHC class II proteins. Each HLA class I gene has eight exons, the first seven each encodes different part of the protein (Exon 1—Leader peptide; Exon 2—alpha1 domain; Exon 3—alpha2 domain; Exon 4—alpha3 domain; Exon 5—Transmembrane region; Exon 6—Cytoplasmic tail; Exon 7—Cytoplasmic tail). Exons 2 and 3 are the most important because they encode for the binding core of the HLA molecule and are also the most polymorphic regions (FIGS. 1A, 1B, and 1C).

The classical HLA class I genes encode polymorphic cell surface proteins expressed on most nucleated cells. The natural function of these proteins is to bind and present diverse sets of peptide fragments from intracellularly processed antigens to the T cell antigen receptors (TCRs). Thus, the peptide-binding capacity of the MHC molecule facilitates immune recognition of intracellular pathogens and altered self-proteins. Therefore, by increasing the peptide repertoire for TCRs, the polymorphism of MHC molecules plays a critical role in the immune response potential of a host. On the other hand, MHC polymorphism exerts an immunological burden on the host transplanted with allogeneic tissues. As a result, mismatches in HLA class I molecules are one of the main causes of allograft rejection and graft versus host disease, and the level of HLA matching between tissue donor and recipient is a major factor in the success of allogeneic tissue and marrow transplants. It is therefore a matter of considerable medical significance to be able to determine the "type" of the HLA class I genes of candidate organ donors and recipients.

HLA class I histocompatibility antigens for patient-donor matching are conventionally determined by serological typing. Biochemical and molecular techniques have revealed that HLA class I polymorphism is far greater than previously recognized by conventional methods.

The number of newly identified HLA alleles have been increasing over time with nearly 15.000 HLA class I alleles and over 5,000 HLA class II alleles identified as of 2018. To date, about 4,638 different HLA-A allelic sequences, 5,590 different HLA-B allelic sequences, and 4,374 different HLA-C allelic sequences have been identified. These different allelic sequences encode for about 3.172 HLA-A proteins, 3,923. HLA-B proteins, and 2,920 HLA-C proteins. This high level of allelic diversity complicates the typing of the HLA class I genes. Thus, HLA typing at the nucleic acid level is a formidable task. Allelic diversity within any one gene means that a great many probes need to be developed if hybridization-based tests are used in the typing. Further, the general applicability of DNA typing methods to HLA genes depends on the design of primers that provide effective locus-specific amplification of one HLA gene.

Quantifying HLA Diversity

In some embodiments, provided herein are systems and methods to quantify HLA allele diversity. In some embodiments, diversity scores are calculated for all pairwise HLA alleles by calculating the percentile of the alignment score of a given pair of HLA allele in a distribution of all pairwise alignment scores.

In some embodiments, a method of quantifying a diversity of at least one HLA allele pair in a subject comprises obtaining DNA sequences of one or more HLA allele pairs in the subject, comparing the DNA sequences of the one or more HLA allele pairs to obtain alignment scores, obtaining a distribution of the alignment scores for the one or more HLA allele pairs, and determining a percentile score for the at least one HLA allele pair relative to the distribution of the alignment scores for all HLA allele pairs.

In some embodiments, the method of quantifying a diversity of at least one HLA allele pair further comprises comparing the percentile score to a first predetermined threshold.

In some embodiments of the method of quantifying a diversity of at least one HLA allele pair, the at least one HLA allele pair comprises any pair of HLA A, B, C, E, F, G, H, J, K, L, DP, DQ, and DR alleles.

In some embodiments of the method of quantifying a diversity of at least one HLA allele pair, the at least one HLA allele pair comprises an allele from any of the rows combined with an allele from any of the columns in TABLE 1.

TABLE 1

| Allele pair combinations | | | | | | | | | | | | | |
|---|---|---|---|---|---|---|---|---|---|---|---|---|---|
| | A | B | C | E | F | G | H | J | K | L | DP | DQ | DR |
| A | x | x | x | x | x | x | x | x | x | x | x | x | x |
| B | x | x | x | x | x | x | x | x | x | x | x | x | x |
| C | x | x | x | x | x | x | x | x | x | x | x | x | x |
| E | x | x | x | x | x | x | x | x | x | x | x | x | x |
| F | x | x | x | x | x | x | x | x | x | x | x | x | x |
| G | x | x | x | x | x | x | x | x | x | x | x | x | x |
| H | x | x | x | x | x | x | x | x | x | x | x | x | x |
| J | x | x | x | x | x | x | x | x | x | x | x | x | x |
| K | x | x | x | x | x | x | x | x | x | x | x | x | x |
| L | x | x | x | x | x | x | x | x | x | x | x | x | x |
| DP | x | x | x | x | x | x | x | x | x | x | x | x | x |
| DQ | x | x | x | x | x | x | x | x | x | x | x | x | x |
| DR | x | x | x | x | x | x | x | x | x | x | x | x | x |

In some embodiments, any of the allele combinations listed in TABLE 1 can be combined one or more additional parameters in an embodiment of a method of quantifying HLA diversity as provided herein. Non-limiting examples of additional parameters include RNA and/or protein expression levels of the HLA alleles, HLA zygosity, familial genetic traits, hereditary genetic traits, Mendelian inheritance traits, non-Mendelian inheritance traits, other genetic associations and correlations, such as tumor mutational burden (TMB), neoantigen load, microsatellite instability, tumor microenvironment, T cell receptor repertoire diversity.

In some embodiments, one or more additional parameters include a mutational load of a tumor and/or a cancer in an embodiment of a method of quantifying HLA diversity as provided herein. As used herein, "mutational load of a tumor and/or a cancer" (also referred to herein as "mutational load" or "tumor burden score" or TMB) refers to the total number of somatic coding mutations in tumor and/or a cancer genome.

Without being limited by any particular theory, it is believed that higher TMB increases the probability of neoantigen recognition by cytotoxic T cells.

In some embodiments, one or more additional parameters include age of the patient, gender, stage of tumor, type of cancer, infection history of patient and cancer treatment regimens.

In some embodiments of the method of quantifying a diversity of at least one HLA allele pair, if the percentile score is equal to or greater than the first predetermined threshold, the subject is recommended a first treatment.

As used herein, "percentile score" is defined as a measure indicating the value below which a given percentage of observations in a group of observations fall. For example, if an alignment of a pair of HLA alleles, or allele domains, yields a percentile score of 95, then that pair of HLA alleles are more similar to each other than 95% of all pairs of HLA alleles or domains in the group of alleles analyzed. On the other hand, if an alignment of a pair of HLA alleles yields a percentile score of 5, then that pair of HLA alleles or domains are more similar to each other than just 5% of all pairs of HLA alleles or domains in the group of alleles analyzed.

As used herein, "predetermined threshold" is a threshold value based on the HLA percentile score. The predetermined threshold can vary based on an embodiment of the method of quantifying HLA diversity. For example, the predetermined threshold can vary depending on the number of additional parameters included in an embodiment of a method of quantifying HLA diversity.

In some embodiment, the subject is a human. In some embodiments, the methods and systems provided herein can be extrapolated to other organisms. Non-limiting examples include, non-human primates, rats, mice, dogs, cats, guinea pigs, cattle, etc.

Non-limiting examples of tumor/cancer include breast adenocarcinoma, pancreatic adenocarcinoma, lung carcinoma, prostate cancer, glioblastoma multiform, hormone refractory prostate cancer, solid tumor malignancies such as colon carcinoma, non-small cell lung cancer (NSCLC), anaplastic astrocytoma, bladder carcinoma, sarcoma, ovarian carcinoma, rectal hemangiopericytoma, pancreatic carcinoma, advanced cancer, cancer of large bowel, stomach, pancreas, ovaries, melanoma pancreatic cancer, colon cancer, bladder cancer, hematological malignancies, squamous cell carcinomas, breast cancer, glioblastoma, or any neoplasm associated with brain including, but not limited to, astrocytomas (e.g., pilocytic astrocytoma, diffuse astrocytoma, anaplastic astrocytoma, and brain stem gliomas), glioblastomas (e.g., glioblastomas multiforme), meningioma, other gliomas (e.g., ependymomas, oligodendrogliomas, and mixed gliomas), and other brain tumors (e.g., pituitary tumors, craniopharyngiomas, germ cell tumors, pineal region tumors, medulloblastomas, and primary CNS lymphomas). In some embodiments, the tumor/cancer is related to one or more types of tumor/cancer provided herein.

In some embodiments, a first treatment comprises an immune checkpoint inhibitor (ICI). In some embodiments, an ICI stimulates cytotoxic lymphocyte activity against tumor and/or cancer cells.

In some embodiments, a first treatment comprises an ICI selected from the group consisting of P D-1 inhibitors, PDL-1 inhibitors, and CTLA-4 inhibitors.

In some embodiments, a first treatment comprises one or more ICI selected from the group consisting of PD-1 inhibitors, PDL-1 inhibitors, and CTLA-4 inhibitors.

In some embodiments, a first treatment comprises a combination of ICI selected from the group consisting of PD-1 inhibitors, PDL-1 inhibitors, and CTLA-4 inhibitors.

In some embodiments, a first treatment comprises an ICI selected from the group consisting of Pembrolizumab (Keytruda), Nivolumab (Opdivo), Cemiplimab (Libtayo)

Atezolizumab (Tecentriq), Avelumab (Bavencio), Durvalumab (Imfinzi), and Ipilimumab (Yervoy).

In some embodiments, a first treatment comprises one or more ICI selected from the group consisting of Pembrolizumab (Keytruda), Nivolumab (Opdivo), Cemiplimab (Libtayo) Atezolizumab (Tecentriq), Avelumab (Bavencio), Durvalumab (Imfinzi), and Ipilimumab (Yervoy).

In some embodiments, a first treatment comprises a combination of ICI selected from the group consisting of Pembrolizumab (Keytruda), Nivolumab (Opdivo), Cemiplimab (Libtayo) Atezolizumab (Tecentriq), Avelumab (Bavencio), Durvalumab (Imfinzi), and Ipilimumab (Yervoy).

In some embodiments, if the percentile score is less than the first predetermined threshold, the subject is not recommended a second treatment.

In some embodiments, a second treatment comprises a non-ICI.

In some embodiments, a second treatment comprises any treatment other than PD-1 inhibitors, PDL-1 inhibitors, and CTLA-4 inhibitors.

In some embodiments, a second treatment comprises any treatment other than Pembrolizumab (Keytruda), Nivolumab (Opdivo), Cemiplimab (Libtayo) Atezolizumab (Tecentriq), Avelumab (Bavencio), Durvalumab (Imfinzi), and Ipilimumab (Yervoy).

In some embodiments, a second treatment comprises a treatment selected from the group consisting of surgery, radiation therapy, chemotherapy, immunotherapy, targeted therapy, hormone therapy, stem cell transplant, cytokine therapy, gene therapy, cell therapy, phototherapy, thermotherapy, and sound therapy.

In some embodiments, the method of quantifying a diversity of at least one HLA allele pair, the method further comprises determining an RNA expression levels of the one or more HLA allele pairs, obtaining an RNA expression level score of the at least one HLA allele pair relative to the expression levels of the one or more HLA allele pairs, determining a weighted percentile score for the at least one HLA allele pair, based on the RNA expression level score of the at least one HLA allele pair, relative to the distribution of the alignment scores for the one or more HLA allele pairs, and comparing the weighted percentile score to second predetermined threshold.

In some embodiments, the method of quantifying a diversity of at least one HLA allele pair, the method further comprises determining an RNA expression levels of the one or more HLA allele pairs.

In some embodiments, the method of quantifying a diversity of at least one HLA allele pair, the method further comprises determining an RNA expression levels of the one or more HLA allele pairs, and obtaining an RNA expression level score of the at least one HLA allele pair relative to the expression levels of the one or more HLA allele pairs.

In some embodiments, the method of quantifying a diversity of at least one HLA allele pair, the method further comprises determining an RNA expression levels of the one or more HLA allele pairs, and obtaining an RNA expression level score of the at least one HLA allele pair relative to the expression levels of the one or more HLA allele pairs, and determining a weighted percentile score for the at least one HLA allele pair.

In some embodiments, the method of quantifying a diversity of at least one HLA allele pair, the method further comprises determining an RNA expression levels of the one or more HLA allele pairs, and obtaining an RNA expression level score of the at least one HLA allele pair relative to the expression levels of the one or more HLA allele pairs, and determining a weighted percentile score for the at least one HLA allele pair, based on the RNA expression level score of the at least one HLA allele pair.

In some embodiments, the method of quantifying a diversity of at least one HLA allele pair, the method further comprises determining an RNA expression levels of the one or more HLA allele pairs, and obtaining an RNA expression level score of the at least one HLA allele pair relative to the expression levels of the one or more HLA allele pairs, and determining a weighted percentile score for the at least one HLA allele pair, based on the RNA expression level score of the at least one HLA allele pair, relative to the distribution of the alignment scores for the one or more HLA allele pairs.

In some embodiments, the method of quantifying a diversity of at least one HLA allele pair, the method further comprises determining an RNA expression levels of the one or more HLA allele pairs, and obtaining an RNA expression level score of the at least one HLA allele pair relative to the expression levels of the one or more HLA allele pairs, and determining a weighted percentile score for the at least one HLA allele pair, based on the RNA expression level score of the at least one HLA allele pair, relative to the distribution of the alignment scores for the one or more HLA allele pairs, and comparing the weighted percentile score to second predetermined threshold.

In some embodiments, RNA expression levels of HLA alleles can be determined and quantified using one or more of microarray analysis, real time PCR, quantitative real time PCR, reverse transcription PCR, RNA Seq, NextGen sequencing, tiling array, northern blotting, SAGE, in situ hybridization, and expressed sequence tags, and other RNA quantifying techniques known in the art.

In some embodiments, protein expression levels of HLA alleles can be determined and quantified using one or more of western blotting, mass spectrometry, and other protein quantifying techniques known in the art.

In some embodiments, if the weighted percentile score is equal to or greater than the second predetermined threshold, the subject is recommended a first treatment.

In some embodiments, if the weighted percentile score is less than the second predetermined threshold, the subject is recommended a second treatment.

In some embodiments, the first predetermined threshold is 50%. In some embodiments, the first predetermined threshold is 75%. In some embodiments, the first predetermined threshold is 25%. In some embodiments, the first predetermined threshold is 50% with at least one additional parameters included in an embodiment of a method of quantifying HLA diversity. In some embodiments, the first predetermined threshold is 75% with at least one additional parameters included in an embodiment of a method of quantifying HLA diversity. In some embodiments, the first predetermined threshold is 25% with at least one additional parameters included in an embodiment of a method of quantifying HLA diversity. In some embodiments, the first predetermined threshold ranges from about 10% to about 90%.

In some embodiments, the second predetermined threshold is 50%. In some embodiments, the second predetermined threshold is 75%. In some embodiments, the second predetermined threshold is 25%. In some embodiments, the second predetermined threshold is 50% with at least one additional parameters included in an embodiment of a method of quantifying HLA diversity. In some embodiments, the second predetermined threshold is 75% with at least one additional parameters included in an embodiment of a method of quantifying HLA diversity. In some embodiments, the second predetermined threshold is 25% with at least one additional parameters included in an embodiment of a method of quantifying HLA diversity. In some embodiments, the second predetermined threshold ranges from about 10% to about 90%.

In some embodiments, a first treatment comprises an immune checkpoint inhibitor (ICI). In some embodiments, an ICI stimulates cytotoxic lymphocyte activity against tumor and/or cancer cells.

In some embodiments, a first treatment comprises an ICI selected from the group consisting of PD-1 inhibitors, PDL-1 inhibitors, and CTLA-4 inhibitors.

In some embodiments, a first treatment comprises one or more ICI selected from the group consisting of PD-1 inhibitors, PDL-1 inhibitors, and CTLA-4 inhibitors.

In some embodiments, a first treatment comprises a combination of ICI selected from the group consisting of PD-1 inhibitors, PDL-1 inhibitors, and CTLA-4 inhibitors.

In some embodiments, a first treatment comprises an ICI selected from the group consisting of Pembrolizumab (Keytruda), Nivolumab (Opdivo), Cemiplimab (Libtayo) Atezolizumab (Tecentriq), Avelumab (Bavencio), Durvalumab (Imfinzi), and Ipilimumab (Yervoy).

In some embodiments, a first treatment comprises one or more ICI selected from the group consisting of Pembrolizumab (Keytruda), Nivolumab (Opdivo), Cemiplimab (Libtayo) Atezolizumab (Tecentriq), Avelumab (Bavencio), Durvalumab (Imfinzi), and Ipilimumab (Yervoy).

In some embodiments, a first treatment comprises a combination of ICI selected from the group consisting of Pembrolizumab (Keytruda), Nivolumab (Opdivo), Cemiplimab (Libtayo) Atezolizumab (Tecentriq), Avelumab (Bavencio), Durvalumab (Imfinzi), and Ipilimumab (Yervoy).

In some embodiments, a second treatment comprises a non-ICI.

In some embodiments, a second treatment comprises any treatment other than PD-1 inhibitors, PDL-1 inhibitors, and CTLA-4 inhibitors.

In some embodiments, a second treatment comprises any treatment other than Pembrolizumab (Keytruda), Nivolumab (Opdivo), Cemiplimab (Libtayo) Atezolizumab (Tecentriq), Avelumab (Bavencio), Durvalumab (Imfinzi), and Ipilimumab (Yervoy).

In some embodiments, a second treatment comprises a treatment selected from the group consisting of surgery, radiation therapy, chemotherapy, immunotherapy, targeted therapy, hormone therapy, stem cell transplant, cytokine therapy, gene therapy, cell therapy, phototherapy, thermotherapy, and sound therapy.

In some embodiments, is the first predetermined threshold is 50%, then the subject further recommended a first additional treatment. In some embodiments, if the first predetermined threshold is 75%, then the subject is further recommended a first additional treatment. In some embodiments, if the first predetermined threshold is 25%, then the subject is further recommended a first additional treatment. In some embodiments, the first predetermined threshold is 50% with at least one additional parameters included in an embodiment of a method of quantifying HLA diversity, then the subject is further recommended a first additional treatment. In some embodiments, the first predetermined threshold is 75% with at least one additional parameters included in an embodiment of a method of quantifying HLA diversity, then the subject is further recommended a first additional treatment. In some embodiments, the first predetermined threshold is 25% with at least one additional parameters included in an embodiment of a method of quantifying HLA diversity, then the subject is further recommended a first additional treatment. In some embodiments, the first predetermined threshold ranges from about 10% to about 90%.

In some embodiments, a first additional treatment comprises an ICI selected from the group consisting of PD-1 inhibitors, PDL-1 inhibitors, and CTLA-4 inhibitors.

In some embodiments, a first additional treatment comprises one or more ICI selected from the group consisting of PD-1 inhibitors, PDL-1 inhibitors, and CTLA-4 inhibitors.

In some embodiments, a first additional treatment comprises a combination of ICI selected from the group consisting of PD-1 inhibitors, PDL-1 inhibitors, and CTLA-4 inhibitors.

In some embodiments, a first additional treatment comprises an ICI selected from the group consisting of Pembrolizumab (Keytruda), Nivolumab (Opdivo), Cemiplimab (Libtayo) Atezolizumab (Tecentriq), Avelumab (Bavencio), Durvalumab (Imfinzi), and Ipilimumab (Yervoy).

In some embodiments, a first additional treatment comprises one or more ICI selected from the group consisting of Pembrolizumab (Keytruda), Nivolumab (Opdivo), Cemiplimab (Libtayo) Atezolizumab (Tecentriq), Avelumab (Bavencio), Durvalumab (Imfinzi), and Ipilimumab (Yervoy).

In some embodiments, a first additional treatment comprises a combination of ICI selected from the group consisting of Pembrolizumab (Keytruda), Nivolumab (Opdivo), Cemiplimab (Libtayo) Atezolizumab (Tecentriq), Avelumab (Bavencio), Durvalumab (Imfinzi), and Ipilimumab (Yervoy).

In some embodiments, is the second predetermined threshold is 50%, then the subject further recommended a second additional treatment. In some embodiments, if the second predetermined threshold is 75%, then the subject is further recommended a second additional treatment. In some embodiments, if the second predetermined threshold is 25%, then the subject is further recommended a second additional treatment. In some embodiments, the second predetermined threshold is 50% with at least one additional parameters included in an embodiment of a method of quantifying HLA diversity, then the subject is further recommended a second additional treatment. In some embodiments, the second predetermined threshold is 75% with at least one additional parameters included in an embodiment of a method of quantifying HLA diversity, then the subject is further recommended a second additional treatment. In some embodiments, the second predetermined threshold is 25% with at least one additional parameters included in an embodiment of a method of quantifying HLA diversity, then the subject is further recommended a second additional treatment. In some embodiments, the second predetermined threshold ranges from about 10% to about 90%.

In some embodiments, a second additional treatment comprises a non-ICI.

In some embodiments, a second additional treatment comprises any treatment other than PD-1 inhibitors, PDL-1 inhibitors, and CTLA-4 inhibitors.

In some embodiments, a second additional treatment comprises any treatment other than Pembrolizumab (Keytruda), Nivolumab (Opdivo), Cemiplimab (Libtayo) Atezolizumab (Tecentriq), Avelumab (Bavencio), Durvalumab (Imfinzi), and Ipilimumab (Yervoy).

In some embodiments, a second treatment comprises a treatment selected from the group consisting of surgery, radiation therapy, chemotherapy, immunotherapy, targeted therapy, hormone therapy, stem cell transplant, cytokine therapy, gene therapy, cell therapy, phototherapy, thermotherapy, and sound therapy.

In some embodiments, the method of quantifying a diversity of at least one HLA allele pair, the quantifying is repeated over time to determine if there is a change in the percentile score relative to the first predetermined threshold.

In some embodiments, the method of quantifying a diversity of at least one HLA allele pair, the quantifying is repeated over time to determine if there is a change in the percentile score relative to the second predetermined threshold.

In some embodiments, an assessment of TCR clonality is included in the HLA diversity analysis.

In some embodiments, a method of determining the predicted efficacy of a cancer treatment in a patient comprises calculating a hazard ratio of HLA allele pairs in the patient, the hazard ratio reflecting the allelic diversity of the HLA allele pairs in the patient, comparing the hazard ratio to a predetermined threshold, a hazard ratio above the predetermined threshold indicating that the patient is predicted to have a high efficacy for a cancer treatment, and a hazard ratio below the predetermined threshold indicating that the patient is predicted to have a low efficacy for a cancer treatment.

As used herein, "hazard ratio" (HR) is a probability of a "hazard" to a population (e.g., disease, debilitation, death, unresponsiveness to a treatment, etc.) determined as a statistics-based correlation between diversity of the HLA alleles and one or more additional parameters as provided herein. For example, in the context of responsiveness to an anti-cancer/tumor treatment, a lower hazard ratio would indicate a greater responsiveness to treatment, and a higher hazard ratio would indicate a lower responsiveness to treatment.

In some embodiments, a method of determining the predicted efficacy of a cancer treatment in a patient is provided.

In some embodiments, a method of determining the predicted efficacy of a cancer treatment in a patient comprises calculating a hazard ratio of HLA allele pairs in the patient.

In some embodiments, a method of determining the predicted efficacy of a cancer treatment in a patient comprises calculating a hazard ratio of HLA allele pairs in the patient, the hazard ratio reflecting the allelic diversity of the HLA allele pairs in the patient.

In some embodiments, a method of determining the predicted efficacy of a cancer treatment in a patient comprises calculating a hazard ratio of HLA allele pairs in the patient, the hazard ratio reflecting the allelic diversity of the HLA allele pairs in the patient, and comparing the hazard ratio to a predetermined threshold.

In some embodiments, a method of determining the predicted efficacy of a cancer treatment in a patient comprises calculating a hazard ratio of HLA allele pairs in the patient, the hazard ratio reflecting the allelic diversity of the HLA allele pairs in the patient, comparing the hazard ratio to a predetermined threshold, a hazard ratio above the predetermined threshold indicates that the patient is predicted to have a high efficacy for a cancer treatment.

In some embodiments, a method of determining the predicted efficacy of a cancer treatment in a patient comprises calculating a hazard ratio of HLA allele pairs in the patient, the hazard ratio reflecting the allelic diversity of the HLA allele pairs in the patient, comparing the hazard ratio to a predetermined threshold, a hazard ratio below the predetermined threshold indicates that the patient is predicted to have a low efficacy for a cancer treatment.

In some embodiments of a method of determining the predicted efficacy of a cancer treatment in a patient, the cancer is a tumor.

In some embodiments of a method of determining the predicted efficacy of a cancer treatment in a patient, the cancer is a tumor, and further comprises measuring a tumor burden score for the patient.

In some embodiments of a method of determining the predicted efficacy of a cancer treatment in a patient, the cancer is a tumor, and further comprises measuring a tumor burden score for the patient, and comparing the tumor burden score to a predetermined threshold as a factor in determining the efficacy of a cancer treatment.

EXAMPLES

The following examples are non-limiting and other variants within the scope of the art also contemplated.

Example 1—HLA Diversity and Heterozygosity

In this example, the clinical utility of HLA diversity score in conjunction with HLA heterozygosity was determined. In order to test the feasibility of using HLA diversity score as a biomarker to predict a patient's response to ICI treatment based on HLA heterogzygozity, a cohort of 110 patients with metastatic melanoma treated with CTLA-4 (Van Allen, E., et al., (2015) Science, Vol. 350, No. 6257, pp. 207-211, 2015) was selected.

Figure 2A:
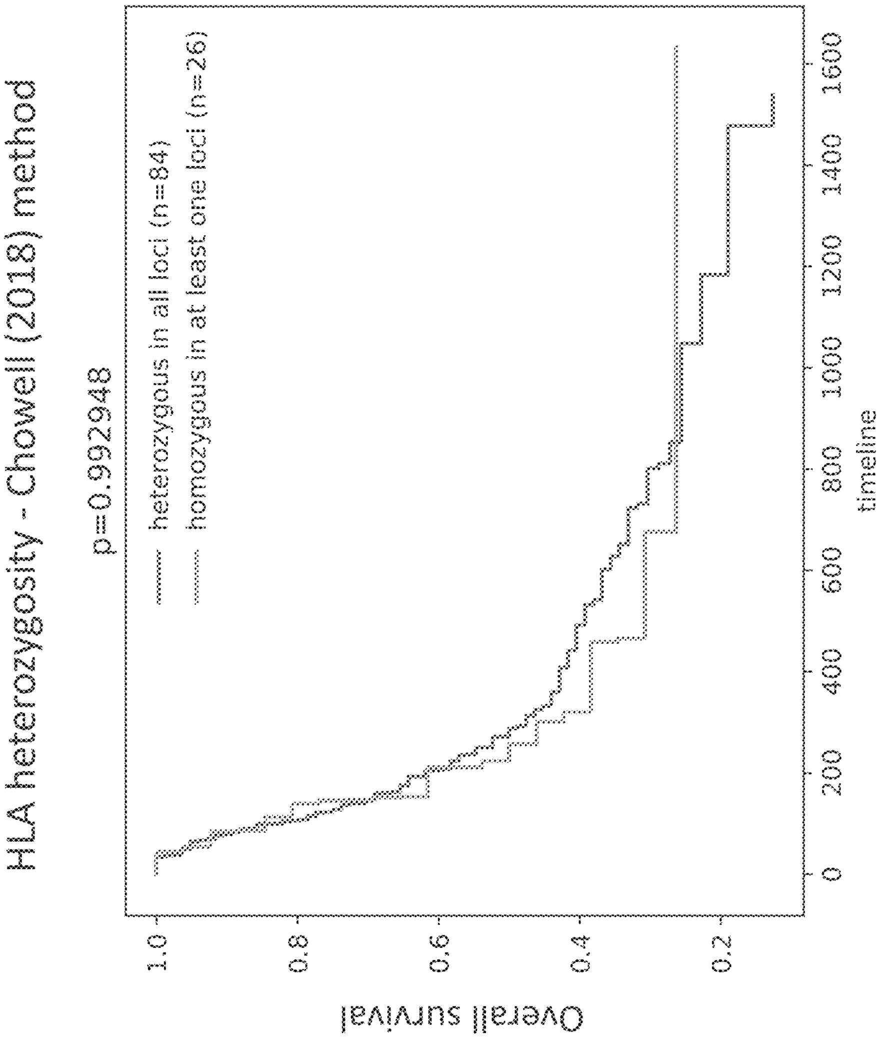
FIG. 2A shows a graph of the results of a determination of HLA diversity score in conjunction with HLA heterozygosity by a method known in the art. The X axis shows timeline in days and Y axis shows overall survival (1=100%).

When using the Chowell method (Chowell, D., et al., Science Vol. 359, No. 6375, pp. 582-587, 2018) to categorize the patients based on HLA heterozygosity only, the two groups of patients, i.e., those who were determined to be HLA heterozygous in all loci versus those who were determined to be homozygous in at least one locus) showed no statistically significant difference in survival (p=0.99; HR=1 (95% Confidence Interval (CI)=0.60-1.68); FIG. 2A). Thus, just measuring whether a patient was homozygous or heterozygous for an HLA allele did not correlate well with a patient's survival after treatment.

However, using embodiments of the methods described herein, a diversity score was calculated for each HLA gene in the same patient population based on a percentile of the alignment score of a given pair of HLA alleles. Thus for each patient, three diversity scores were calculated: one each for HLA-A, HLA-B and HLA-C to determine how different their alleles were from one another. Next patients were categorized into two groups, with the first group having at least one HLA locus within the top 20% of diversity, and the second group with the lower 80% of HLA diversities in all three HLA-A, HLA-B and HLA-C loci.

Figure 2B:
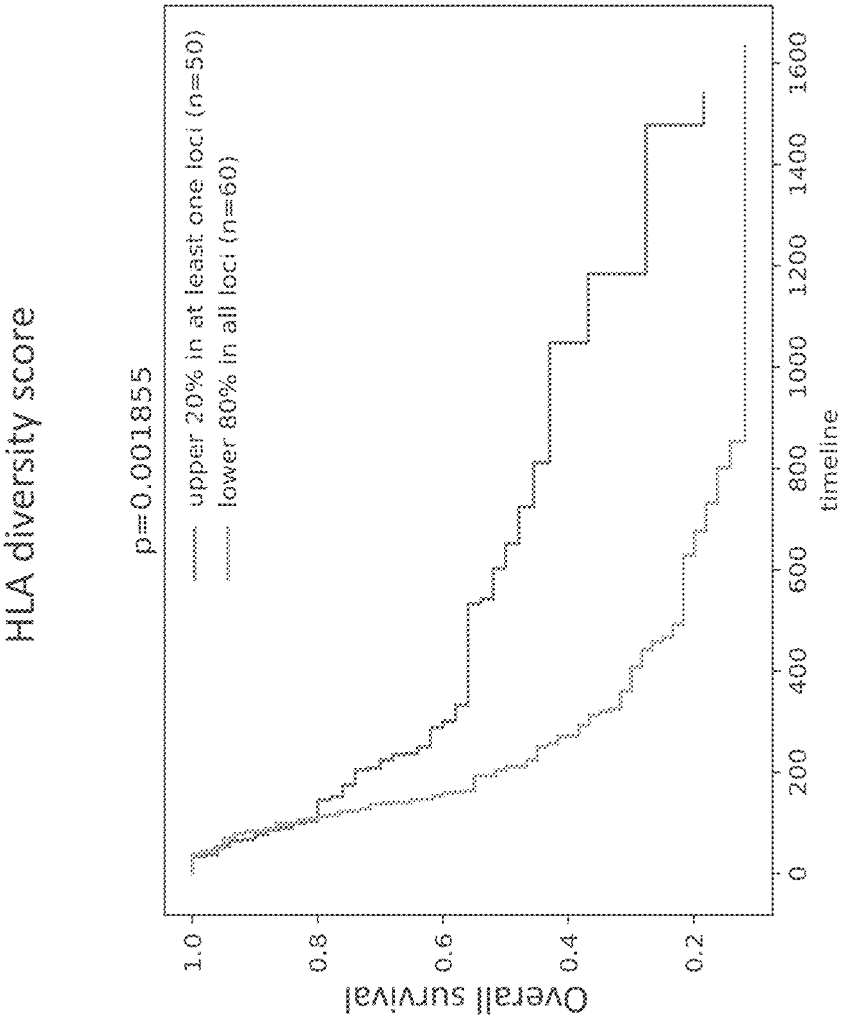
FIG. 2B shows a graph of the results of a determination of HLA diversity score in conjunction with HLA heterozygosity by an embodiment of a method of quantifying HLA diversity according to the present disclosure. The X axis shows timeline in days and Y axis shows overall survival (1=100%).

In contrast to Chowell method, when the method described herein to quantify the HLA diversity score was used to categorize the patients, patients with upper 20% diversity score in at least one loci (n=50), and patients with low 80% diversity score in all loci (n=60), the two groups of patients showed statistically significantly different overall survival (p<0.01, HR=2.01 (95% CI=1.28-3.19); FIG. 2B).

These data demonstrate the applicability of the methods and systems described herein to use an HLA diversity score to differentiate patients based on their HLA heterozygosity, and the utility of this approach as a biomarker to predict a patient's response to ICI treatment.

Example 2—HLA Diversity, HLA Heterozygosity, and TMB

In this example, the clinical utility of HLA diversity score in conjunction with HLA heterozygosity and Tumor Mutation Burden (TMB) was determined.

In order to test the feasibility of using HLA diversity score as a biomarker to predict a patient's response to ICI treatment based on HLA heterogzygozity and TMB, publicly available data on a cohort of 61 patients was used.

Figure 3A:
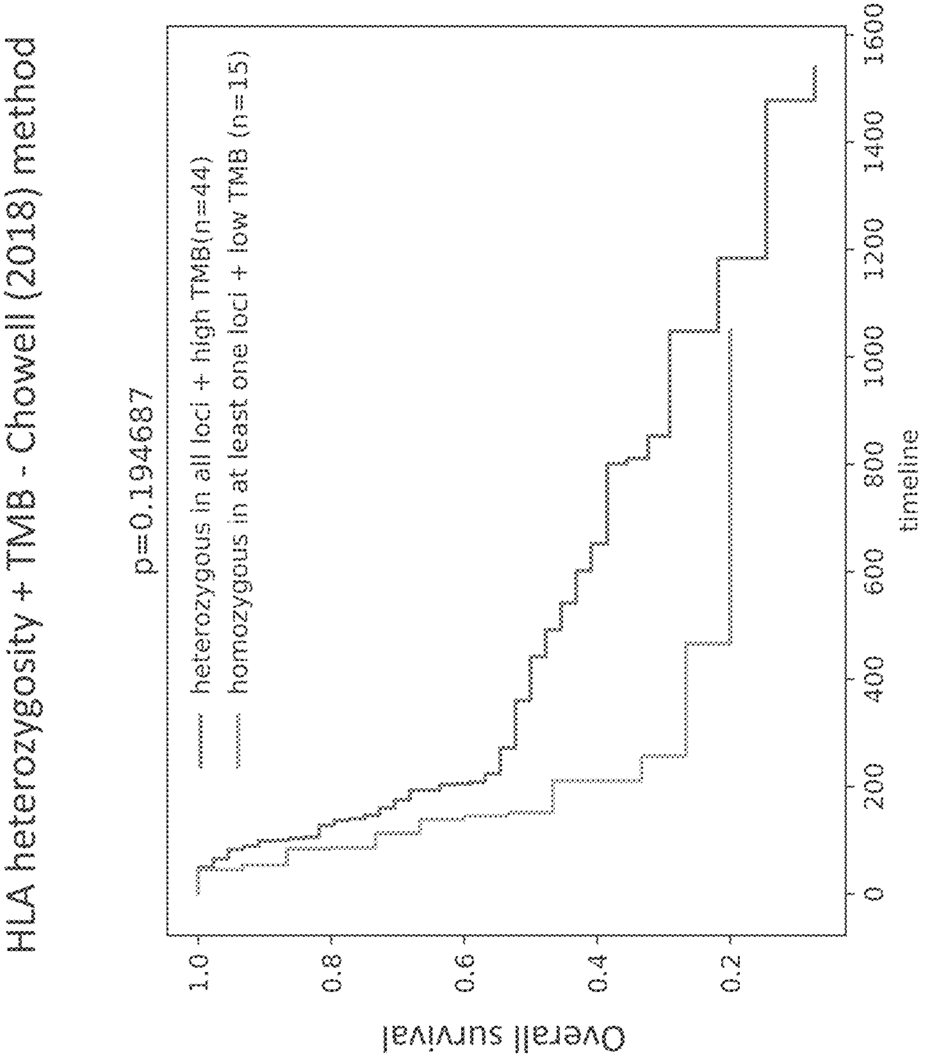
FIG. 3A shows a graph of the results of a determination of HLA diversity score in conjunction with HLA heterozygosity and TMB by a method known in the art. The X axis shows timeline in days and Y axis shows overall survival (1=100%).

When using the Chowell method (Chowell, D., et al., *Science* Vol. 359, No. 6375, pp. 582-587, 2018) to categorize the patients based on HLA heterozygosity and TMB, the two groups of patients, i.e., those who are HLA heterozygous in all loci versus those who are homozygous in at least one locus) showed no statistically significant difference in survival (p=0.19; HR=1.55 (95% CI=0.79-3.03); FIG. 3A).

Based on the embodiments of the methods described herein, a diversity score was calculated for each HLA gene based on a percentile of the alignment score of a given pair of HLA alleles. Thus for each patient, three diversity scores were calculated: one each for HLA-A, HLA-B and HLA-C. Next the patients were categorized into two groups, with the first group having at least one HLA locus within the top 20% diversity, and the second group with the lower 80% HLA diversities in all three HLA-A, HLA-B and HLA-C loci.

Figure 3B:
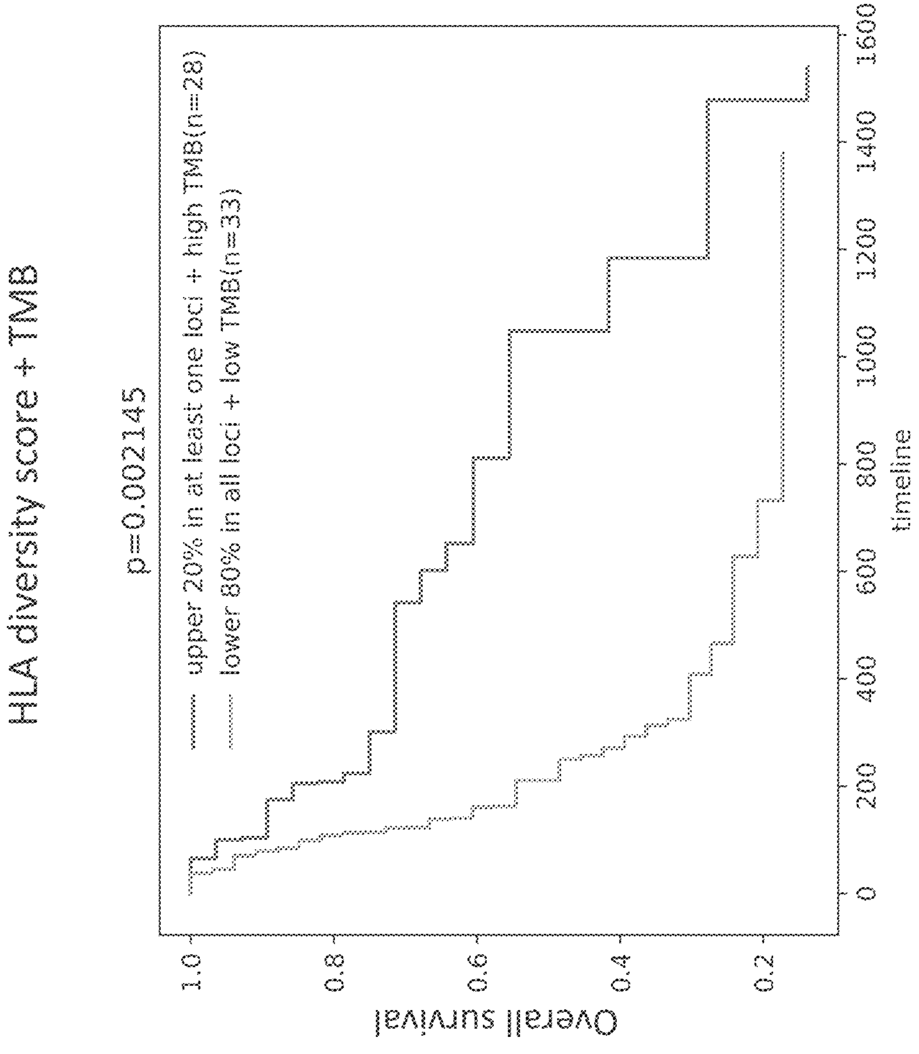
FIG. 3B shows a graph of the results of a determination of HLA diversity score in conjunction with HLA heterozygosity and TMP by an embodiment of a method of quantifying HLA diversity according to the present disclosure. The X axis shows timeline in days and Y axis shows overall survival (1=100%).

In contrast to Chowell method, when the method described herein to quantify the HLA diversity score was used to categorize the patients, patients with upper 20% diversity score in at least one loci and high TMB (n=28), and patients with low 80% diversity score in all loci and low TMB (n=33), the two groups of patients showed statistically significantly different overall survival (p<0.002, HR=2.69 (95% CI=1.39-5.21); FIG. 3B).

These data demonstrate the applicability of the systems and methods described herein to quantify the HLA diversity score to differentiate patients based on the HLA heterozygosity and TMB, and its utility as a biomarker to predict a patient's response to ICI treatment.

Example 3—TMB and Overall Survival

In this example, the correlation between TMB and overall survival was assessed.

Publicly available data on a cohort of 110 patients was used. The patients were categorized into two groups, using the median TMB level (200 total mutation per patient) as the cutoff, into high TMB and low TMB groups.

Figure 4:
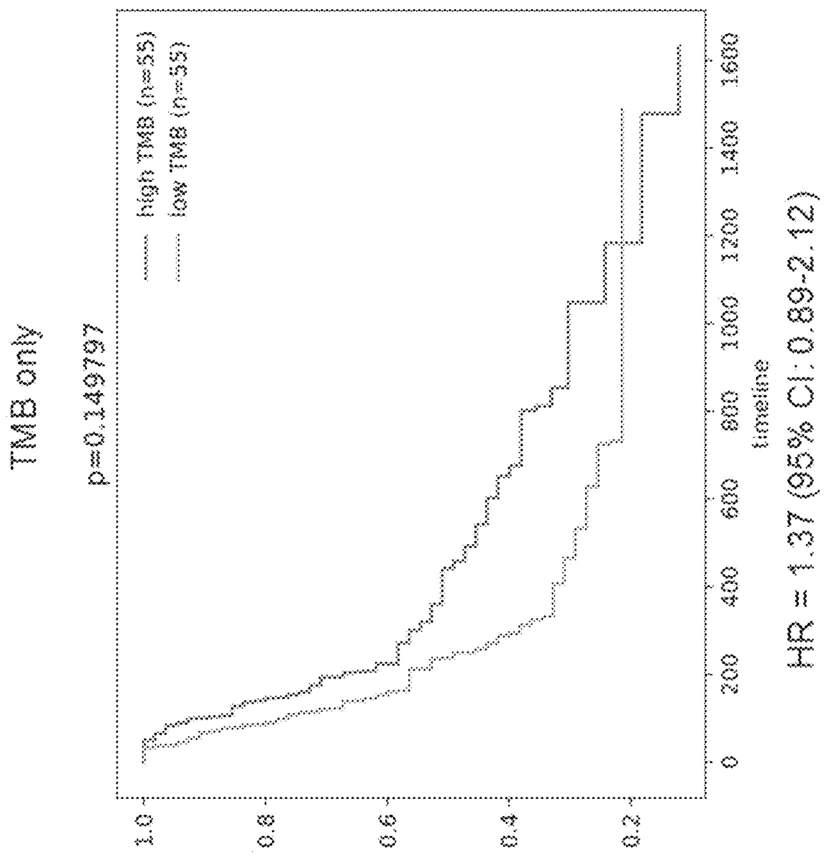
FIG. 4 shows a graph of correlation between TMB and overall survival. The X axis shows timeline in days and Y axis shows overall survival (1=100%).

High TMB patients showed higher overall survival as compared to low TMB patients (p=0.15, HR=1.37 (95% CI=0.89-2.12); FIG. 4). This may be due to the fact that a higher TMB increases the probability of neoantigen recognition by cytotoxic T cells.

Example 4

A first patient presents with a tumor in their prostate. An analysis is made of his HLA allelic variants. It's discovered that he has HLA alleles A*01:01 and A*01:02 which have a percentage similarity of 99.74%. This means they are more similar than 99.74% of all pairs of known HLA-A alleles, suggesting that they have a very high similarity. This patient is ranked as having a lower chance of a successful CAR-T therapy due to the similarity of the HLA alleles.

A second patient presents with a tumor in their prostate. An analysis is made of their HLA allelic variants. It's discovered that he has HLA alleles A*01:01 and A*24:34 which only have a percentage similarity of 17.97%, suggesting they have low similarity and high diversity. This patient is ranked as compared to the first patient, as having a relatively higher chance of a successful CAR-T therapy to treat the tumor due to the diversity between the HLA alleles.

Example 5

A patient presents with a tumor and is measured to determine their HLA allelic diversity to determine whether various treatments have a high or low chance of success. Instead of only scoring the patients HLA allelic diversity as being within the two categories of heterozygous or and homozygous for HLA alleles, a more complex analysis is performed. The sequence of the HLA A, B, C, E, F, G, H, J, K, L, DP, DQ, and DR genes for each allele from the patient is determined. A percent identity for each allele pair from each gene is calculated to determine an overall score. A diversity score is then calculated for each allele pair in each gene by calculating the percentile of the alignment score of a given pair of HLA allele in a distribution of all pairwise alignment scores. From this score, the patients are divided using the preset cut-off and the hazard ratio is calculated based on survival rate. Statistical analysis is performed using Log-rank test or Wilcoxon-rank sum test without or without Bonferroni correction. This score yields an overall similarity score of 14.4%, meaning that the alleles are not very similar to one another. This high diversity of the patient's HLA genes can then be used to determine that the patient has a relatively higher propensity to respond to anti-tumor therapies.

Example 6

A patient presents with a tumor and is measured to determine their HLA allelic diversity to determine whether various treatments have a high or low chance of success. Instead of only scoring the patients HLA allelic diversity as being within the two categories of heterozygous or and homozygous for HLA alleles, a more complex analysis is performed. The sequence of the HLA A, B, C, E, F, G, H, J, K, L, DP, DQ, and DR genes for each allele from the patient is determined. As mentioned above, each HLA class I gene has eight exons, but exon 2 (corresponding to the alpha1 domain) and exon 3 (corresponding to the alpha2 domain) encode for the binding core of the HLA molecule and are the most polymorphic regions. This is shown in FIGS. 1A, 1B and 1C for HLA-A. HLA-B and HLA-C genes, respectively. An alignment score for each exon 2 and exon 3 domain from each allele pair is given more weight in calculation of the overall alignment score. A diversity score is then calculated for each allele pair in each gene by calculating the percentile of the alignment score of a given pair of HLA allele in a distribution of all pairwise alignment scores. From this score, the hazard ratio is calculated using the allele diversity score cut-off. Statistical analysis is performed using Log-rank test or Wilcoxon-rank sum test without or without Bonferroni correction. This score yields an overall similarity score of 70.4%, meaning that the alleles are fairly similar to one another. This relatively low diversity of the patient's HLA genes can then be used to determine that the patient has a relatively lower propensity to respond to anti-tumor therapies.

Example 7

A patient presents with a tumor and is measured to determine their HLA allelic diversity to determine whether various treatments have a high or low chance of success. Instead of only scoring the patients HLA allelic diversity as being within the two categories of heterozygous or and homozygous for HLA alleles, a more complex analysis is performed. The sequence of the HLA A, B, C, E, F, G, H, J, K, L, DP, DQ, and DR genes for each allele from the patient is determined. As mentioned above, each HLA class I gene has eight exons, but exon 2 (corresponding to the alpha1 domain) and exon 3 (corresponding to the alpha2 domain) encode for the binding core of the HLA molecule and are the most polymorphic regions. This is shown in FIGS. 1A, 1B and 1C for HLA-A. HLA-B and HLA-C genes, respectively. An alignment score for each exon 2 and exon 3 domain from each allele pair is given more weight in calculation of the overall alignment score. A diversity score is then calculated for each allele pair in each gene by calculating the percentile of the alignment score of a given pair of HLA allele in a distribution of all pairwise alignment scores. From this score, the hazard ratio is calculated using the allele diversity score cut-off. Allele diversity score is used in conjunction with RNA expression level for each allele of HLA A, B, C, E, F, G, H, J, K, L, DP, DQ, and DR genes calculated from RNA expression data from the patient. As a predictor, more weight is given to the allele diversity score of highly expressed alleles of the HLA genes in order to calculate the overall diversity score. Thus, allele diversity score from highly expressed alleles of the HLA genes contributes more to the hazard ratio. Statistical analysis is performed using Log-rank test or Wilcoxon-rank sum test without or without Bonferroni correction. This score yields an overall similarity score of 91.4%, meaning that the alleles are fairly similar to one another. This relatively low diversity of the patient's HLA genes can then be used to determine that the patient has a relatively lower propensity to respond to anti-tumor therapies.

Example 8

A patient presents with a tumor and is measured to determine their HLA allelic diversity to determine whether various treatments have a high or low chance of success. Instead of only scoring the patients HLA allelic diversity as being within the two categories of heterozygous or and homozygous for HLA alleles, a more complex analysis is performed. The sequence of the HLA A, B, C, E, F, G, H, J, K, L, DP, DQ, and DR genes for each allele from the patient is determined. As mentioned above, each HLA class I gene has eight exons, but exon 2 (corresponding to the alpha1 domain) and exon 3 (corresponding to the alpha2 domain) encode for the binding core of the HLA molecule and are the most polymorphic regions. This is shown in FIGS. 1A, 1B and 1C for HLA-A HLA-B and HLA-C genes, respectively. A diversity score is generated for each individual HLA gene alone (HLA A, B, C, E, F, G, H, J, K, L, DP, DQ, and DR genes). A combination of scores for HLA A, B, C, E, F, G, H, J, K, L, DP, DQ, and DR genes is used to arrive at single score for each patient. The scores are weighted equally. The analysis is optionally combined with a weighting factor calculated for one or more of the single gene scores. The weighting factor is based on, for example, relative expression of the genes in tissue, determined by microarray, RNA sequencing analysis, etc. The single gene or HLA A, B, C, E, F, G, H, J, K, L, DP, DQ, and DR genes composite scores is also combined with TMB score to arrive a composite score. In addition, the heterozygosity scores are weighted or combined with the HLA zygosity (homozygous=0; most different=1).

Example 9

A patient presents with a tumor and is measured to determine their HLA allelic diversity to determine whether various treatments have a high or low chance of success. Instead of only scoring the patients HLA allelic diversity as being within the two categories of heterozygous or and homozygous for HLA alleles, a more complex analysis is performed. The sequence of the HLA A, B, C, E, F, G, H, J, K, L, DP, DQ, and DR genes for each allele from the patient is determined. As mentioned above, each HLA class I gene has eight exons, but exon 2 (corresponding to the alpha1 domain) and exon 3 (corresponding to the alpha2 domain) encode for the binding core of the HLA molecule and are the most polymorphic regions. This is shown in FIGS. 1A, 1B and 1C for HLA-A. HLA-B and HLA-C genes, respectively. An alignment score for each exon 2 and exon 3 domain from each allele pair is given more weight in calculation of the overall alignment score. A diversity score is then calculated for each allele pair in each gene by calculating the percentile of the alignment score of a given pair of HLA allele in a distribution of all pairwise alignment scores. From this score, the hazard ratio is calculated using the allele diversity score. Allele diversity score is used in conjunction with one or more additional parameters including HLA zygosity, familial genetic traits, hereditary genetic traits, Mendelian inheritance traits, non-Mendelian inheritance traits, other genetic associations and correlations. As a predictor, more weight is given to the one or more additional parameters based on the extent of their contribution (e.g., non-Mendelian inheritance traits) in order to calculate the overall diversity score. Statistical analysis is performed using Log-rank test or Wilcoxon-rank sum test without or without Bonferroni correction. This score yields an overall similarity score of 5.2%, meaning that the alleles are not fairly similar to one another. This relatively low diversity of the patient's HLA genes can then be used to determine that the patient has a relatively higher propensity to respond to anti-tumor therapies.

Example 10

A patient presents with a tumor and is measured to determine their HLA allelic diversity to determine whether various treatments have a high or low chance of success. Instead of only scoring the patients HLA allelic diversity as being within the two categories of heterozygous or and homozygous for HLA alleles, a more complex analysis is performed. The sequence of the HLA A, B, C, E, F, G, H, J, K, L, DP, DQ, and DR genes for each allele from the patient is determined. As mentioned above, each HLA class I gene has eight exons, but exon 2 (corresponding to the alpha1 domain) and exon 3 (corresponding to the alpha2 domain) encode for the binding core of the HLA molecule and are the most polymorphic regions. This is shown in FIGS. 1A, 1B and 1C for HLA-A. HLA-B and HLA-C genes, respectively. An alignment score for each exon 2 and exon 3 domain from each allele pair is given more weight in calculation of the overall alignment score. A diversity score is then calculated for each allele pair in each gene calculating the percentile of the alignment score of a given pair of HLA allele in a distribution of all pairwise alignment scores. From this score, the hazard ratio is calculated using the allele diversity score. Allele diversity score is used in conjunction with one or more additional parameters including a mutational load of the patient's tumor. As a predictor, more weight is given to the one or more additional parameters based on the extent of their contribution (e.g., more weight is given to the mutational load) in order to calculate the overall diversity score. Statistical analysis is performed using Log-rank test or Wilcoxon-rank sum test without or without Bonferroni correction. This score yields an overall similarity score of 3.1%, meaning that the alleles are not fairly similar to one another. This relatively low diversity of the patient's HLA genes can then be used to determine that the patient has a relatively higher propensity to respond to anti-tumor therapies.

Example 11

A patient presents with a tumor and is measured to determine their HLA allelic diversity to determine whether various treatments have a high or low chance of success. Instead of only scoring the patients HLA allelic diversity as being within the two categories of heterozygous or and homozygous for HLA alleles, a more complex analysis is performed. The sequence of the HLA A, B, C, E, F, G, H, J, K, L, DP, DQ, and DR genes for each allele from the patient is determined. As mentioned above, each HLA class I gene has eight exons, but exon 2 (corresponding to the alpha1 domain) and exon 3 (corresponding to the alpha2 domain) encode for the binding core of the HLA molecule and are the most polymorphic regions. This is shown in FIGS. 1A, 1B and 1C for HLA-A, HLA-B and HLA-C genes, respectively. An alignment score for each exon 2 and exon 3 domain from each allele pair is given more weight in calculation of the overall alignment score. A diversity score is then calculated for each allele pair in each gene by calculating the percentile of the alignment score of a given pair of HLA allele in a distribution of all pairwise alignment scores. From this score, the hazard ratio is calculated using the allele diversity score. Allele diversity score is used in conjunction with one or more additional parameters include RNA and/or protein expression levels for each allele of HLA A, B, C, E, F, G, H, J, K, L, DP, DQ, and DR genes from the patient of the alleles calculated from RNA and/or protein expression data from the patient, HLA zygosity, familial genetic traits, hereditary genetic traits, Mendelian inheritance traits, non-Mendelian inheritance traits, other genetic associations and correlations, and in conjunction with a mutational load of the patient's tumor. As a predictor, more weight is given to the one or more additional parameters based on the extent of their contribution (e.g., more weight is given to the allele diversity score of highly expressed alleles of the HLA genes) in order to calculate the overall diversity score. Statistical analysis is performed using Log-rank test or Wilcoxon-rank sum test without or without Bonferroni correction. This score yields an overall similarity score of 7.4%, meaning that the alleles are not fairly similar to one another. This relatively low diversity of the patient's HLA genes can then be used to determine that the patient has a relatively higher propensity to respond to anti-tumor therapies.

Although this disclosure is in the context of certain embodiments and examples, those skilled in the art will understand that the present disclosure extends beyond the specifically disclosed embodiments to other alternative embodiments and/or uses of the embodiments and obvious modifications and equivalents thereof. In addition, while several variations of the embodiments have been shown and described in detail, other modifications, which are within the scope of this disclosure, will be readily apparent to those of skill in the art based upon this disclosure. It is also contemplated that various combinations or sub-combinations of the specific features and aspects of the embodiments may be made and still fall within the scope of the disclosure. It should be understood that various features and aspects of the disclosed embodiments can be combined with, or substituted for, one another in order to form varying modes or embodiments of the disclosure. Thus, it is intended that the scope of the present disclosure herein disclosed should not be limited by the particular disclosed embodiments described above.

What is claimed is:

1. A method of identifying from a population of subjects a candidate for treatment with an Immune Checkpoint Inhibitor, the method comprising:

obtaining DNA sequences comprising over 20,000 HLA allele pairs in a subject from a database;

comparing the DNA sequences of the over 20,000 HLA allele pairs with the sequence of all HLA allele pairs in the population of subjects;

identifying a first subject in the population with at least one HLA allele pair having a heterozygosity above a first predetermined threshold;

determining if the first subject has a tumor mutational burden of greater than 200 total mutations;

determinging that the first subject has at least one HLA allele pair with a heterozygosity above the first predetermined threshold and a tumor mutation burden greater than 200 total mutations, identifying the first subject as a candidate for Immune Checkpoint Inhibitor treatment; and administering an Immune Checkpoint Inhibitor to the candidate.

2. The method of claim 1, comprising determining a percentile score for the at least one HLA allele pair relative to a distribution of alignment scores for the over 20,000 HLA allele pairs and comparing the percentile score to the first predetermined threshold.

3. The method of claim 1, wherein the at least one HLA allele pair comprises any pair of HLA A, B, C, E, F, G, H, J, K, L, DP, DQ, and DR alleles.

4. The method of claim 2, wherein if the percentile score is equal to or greater than the first predetermined threshold, the subject is recommended the Immune Checkpoint Inhibitor treatment.

5. The method of claim 4, wherein if the percentile score is less than the first predetermined threshold, the subject is recommended an alternative treatment.

6. The method of claim 5, wherein the method further comprises:

determining an expression level of the over 20,000 HLA allele pairs;

obtaining an expression level score of the at least one HLA allele pair relative to the expression levels of the over 20,000 HLA allele pairs;

determining a weighted percentile score for the at least one HLA allele pair, based on the expression level score of the at least one HLA allele pair, relative to the distribution of the alignment scores for the over 20,000 HLA allele pairs;

comparing the weighted percentile score to a second predetermined threshold.

7. The method of claim 6, wherein if the weighted percentile score is equal to or greater than the second predetermined threshold, the subject is recommended the Immune Checkpoint Inhibitor treatment.

8. The method of claim 6, wherein if the weighted percentile score is less than the second predetermined threshold, the subject is recommended the alternative treatment.

9. The method of claim 2, wherein the first predetermined threshold is about 75%.

10. The method of claim 6, wherein the second predetermined threshold is about 75%.

11. The method of claim 5, wherein the alternative treatment comprises a non-Immune Checkpoint Inhibitor.

12. The method of claim 2, if the first predetermined threshold is equal to or greater than 50%, then the subject is further recommended a first additional treatment.

13. The method of claim 6, if the second predetermined threshold is less than 50%, then the subject is further recommended a second additional treatment.

14. The method of claim 6, wherein the expression level is an expression level of RNA, expression level of protein or both.

15. The method of claim 4, further comprising repeatedly quantifying a diversity of the at least one HLA allele pair over time to determine if there is a change in the percentile score relative to the first predetermined threshold.

16. The method of claim 6, further comprising repeatedly quantifying a diversity of the at least one HLA allele pair over time to determine if there is a change in the percentile score relative to the second predetermined threshold.

17. The method of claim 1, further comprising quantifying a diversity of the at least one HLA allele pair based on an assessment of TCR clonality.

18. The method of claim 1, wherein the method is performed for all subjects in the population.

19. The method of claim 1, wherein the all HLA allele pairs in the population of subjects represents over 20,000 HLA allele pairs in each subject of the population of subjects.

20. The method of claim 18, further comprising categorizing the subjects based on a diversity score as either having upper 20% diversity score in at least one loci and high tumor mutational burden (TMB) or having lower 80% diversity score in all loci and low TMB.

21. A method of identifying from a population of subjects a candidate for treatment with an Immune Checkpoint Inhibitor, the method comprising:

obtaining DNA sequences comprising over 20,000 HLA allele pairs in a subject from a database;

comparing the DNA sequences of the over 20,000 HLA allele pairs with the sequence of all HLA allele pairs in the population of subjects;

identifying a first subject in the population with at least one HLA allele pair having a heterozygosity above a first predetermined threshold;

determining if the first subject has a tumor mutational burden of greater than 200 total mutations; and if the first subject has at least one HLA allele pair with a heterozygosity above the first predetermined threshold and a tumor mutation burden greater than 200 total mutations, identifying the first subject as a candidate for Immune Checkpoint Inhibitor treatment.

22. The method of claim 21, wherein the at least one HLA allele pair comprises any pair of HLA A, B, C, E, F, G, H, J, K, L, DP, DQ, and DR alleles.

23. The method of claim 21, wherein the all HLA allele pairs in the population of subjects represents over 20,000 HLA allele pairs in each subject of the population of subjects.

24. The method of claim 21, wherein the method is performed for all subjects in the population.

* * * * *

UNITED STATES PATENT AND TRADEMARK OFFICE

CERTIFICATE OF CORRECTION

PATENT NO. : 12,031,181 B2
APPLICATION NO. : 16/838832
DATED : July 9, 2024
INVENTOR(S) : Bochao Zhang et al.

It is certified that error appears in the above-identified patent and that said Letters Patent is hereby corrected as shown below:

In the Specification

Column 4, Line 2, delete “genes.” and insert -- genes, --.

Column 4, Line 2, delete “HLA-E.” and insert -- HLA-E, --.

Column 4, Line 2, delete “HLA-G.” and insert -- HLA-G, --.

Column 4, Line 3, delete “HLA-J.” and insert -- HLA-J, --.

Column 4, Line 43, delete “15.000” and insert -- 15,000 --.

Column 4, Line 48, delete “3.172” and insert -- 3,172 --.

Column 4, Line 49, delete “3,923.” and insert -- 3,923, --.

Column 6, Line 57, delete “P D-1” and insert -- PD-1 --.

Column 12, Line 29 (approx.), delete “heterogzygozity,” and insert -- heterozygosity, --.

Column 13, Line 9 (approx.), delete “heterogzygozity” and insert -- heterozygosity --.

Column 14, Line 12 (approx.), delete “or and” and insert -- and/or --.

Column 14, Line 38 (approx.), delete “or and” and insert -- and/or --.

Column 14, Line 47, delete “HLA-A.” and insert -- HLA-A, --.

Column 15, Line 3, delete “or and” and insert -- and/or --.

Signed and Sealed this
Fifth Day of November, 2024

Katherine Kelly Vidal

Katherine Kelly Vidal
*Director of the United States Patent and Trademark Office*

Column 15, Line 13 (approx.), delete “HLA-A.” and insert -- HLA-A, --.

Column 15, Line 45, delete “or and” and insert -- and/or --.

Column 15, Line 54 (approx.), delete “HLA-A” and insert -- HLA-A, --.

Column 16, Line 11, delete “or and” and insert -- and/or --.

Column 16, Line 20, delete “HLA-A.” and insert -- HLA-A, --.

Column 16, Line 51, delete “or and” and insert -- and/or --.

Column 17, Line 21, delete “or and” and insert -- and/or --.

In the Claims

Column 18, Line 27, Claim 1, delete “determinging” and insert -- determining --.